United States Patent
Keeble et al.

(10) Patent No.: US 11,160,675 B2
(45) Date of Patent: Nov. 2, 2021

(54) DELIVERY SYSTEM FOR DEPLOYING A SELF-EXPANDING TUBE, AND METHOD OF DEPLOYING A SELF-EXPANDING TUBE

(71) Applicant: Oxford Endovascular Ltd., Oxford (GB)

(72) Inventors: Duncan Keeble, Newbury (GB); George Hsieh, Southampton Hampshire (GB)

(73) Assignee: Oxford Endovascular Ltd., Oxford (GB)

( * ) Notice: Subject to any disclaimer, the term of this patent is extended or adjusted under 35 U.S.C. 154(b) by 102 days.

(21) Appl. No.: 16/577,727

(22) Filed: Sep. 20, 2019

(65) Prior Publication Data
US 2020/0008963 A1    Jan. 9, 2020

Related U.S. Application Data

(63) Continuation of application No. PCT/GB2018/050770, filed on Mar. 23, 2018.

(30) Foreign Application Priority Data

Mar. 24, 2017  (GB) ...................... 1704721

(51) Int. Cl.
*A61F 2/966* (2013.01)
(52) U.S. Cl.
CPC ...... *A61F 2/966* (2013.01); *A61F 2210/0014* (2013.01)
(58) Field of Classification Search
CPC ........................ A61F 2/966; A61F 2210/0014
See application file for complete search history.

(56) References Cited

U.S. PATENT DOCUMENTS

2002/0013599 A1   1/2002   Limon et al.
2003/0093141 A1*  5/2003   Dimatteo ............... A61L 31/10
                                              623/1.13
(Continued)

FOREIGN PATENT DOCUMENTS

DE   10 2010 024085   12/2011
EP        0819411      1/1998
(Continued)

*Primary Examiner* — Richard G Louis
(74) *Attorney, Agent, or Firm* — Levine Bagade Han LLP (57) ABSTRACT

Delivery systems for deploying a self-expanding tube into a blood vessel are disclosed. In one arrangement, a tubular member is provided that is configured for insertion into the blood vessel. An elongate body extends within a lumen of the tubular member. A self-expanding tube is positioned radially between the tubular member and the elongate body. Over at least 50% of the length of the self-expanding tube, at least a portion of the self-expanding tube engages outwardly with the tubular member and inwardly with the elongate body. A longitudinal engagement force acting between the self-expanding tube and the tubular member and a longitudinal engagement force acting between the self-expanding tube and the elongate body are such that, during all stages of deployment of the self-expanding tube in use by longitudinal retraction of the tubular member relative to the elongate body, there is substantially no relative movement longitudinally between the elongate body and any portion of the self-expanding tube that remains in engagement with the elongate body.

14 Claims, 4 Drawing Sheets

(56) References Cited

U.S. PATENT DOCUMENTS

| | | |
|---|---|---|
| 2004/0143272 A1 | 7/2004 | Cully et al. |
| 2004/0167604 A1* | 8/2004 | Stinson ............... A61F 2/95 623/1.12 |
| 2007/0239261 A1 | 10/2007 | Bose et al. |
| 2008/0027528 A1 | 1/2008 | Jagger et al. |
| 2009/0287292 A1 | 11/2009 | Becking et al. |
| 2013/0226276 A1 | 8/2013 | Newell et al. |
| 2013/0261730 A1 | 10/2013 | Bose et al. |
| 2014/0025150 A1 | 1/2014 | Lim |
| 2014/0277351 A1 | 9/2014 | Ridgley et al. |
| 2015/0088242 A1 | 3/2015 | Wubbeling et al. |

FOREIGN PATENT DOCUMENTS

| | | |
|---|---|---|
| WO | WO 2002/056798 | 7/2002 |
| WO | WO 2009/033058 | 3/2009 |
| WO | WO 2010/136558 | 12/2010 |
| WO | WO 2013/162817 | 10/2013 |

\* cited by examiner

DELIVERY SYSTEM FOR DEPLOYING A SELF-EXPANDING TUBE, AND METHOD OF DEPLOYING A SELF-EXPANDING TUBE

CROSS-REFERENCE TO RELATED APPLICATIONS

This application is a continuation of International Patent Application Number PCT/GB2018/050770 filed Mar. 23, 2018, which claims priority to GB Patent Application Number 1704721.8 filed Mar. 24, 2017, the contents of which are incorporated herein by reference in their entirety.

BACKGROUND OF THE INVENTION

The present invention relates to deploying a self-expanding tube, particularly for use in redirecting blood flow away from an aneurismal sac.

An intracranial aneurysm is a weak region in the wall of an artery in the brain, where dilation or ballooning of the arterial wall may occur. Histologically, decreases in the tunica media, the middle muscular layer of the artery, and the internal elastic lamina cause structural defects. These defects, combined with hemodynamic factors, lead to aneurismal out-pouchings. Intracranial aneurysms are quite common diseases with a prevalence ranging from one to five percent among adult population according to autopsy studies. In the US alone, ten to twelve million people may have intracranial aneurysms.

Current methods for treating intracranial aneurysms include surgical clipping and endovascular coiling. In the surgical clipping method, the skull of the patient is opened, and a surgical clip is placed across the neck of the aneurysm to stop blood from flowing into the aneurysm sac. The risk of this method is relatively high, especially for elderly or medically complicated patients. Endovascular coiling is a less invasive method involving placement of one or more coils, delivered through a catheter, into the aneurysm until the sac of the aneurysm is completely packed with coils. It helps to trigger a thrombus inside the aneurysm. Although endovascular coiling is deemed to be safer than surgical clipping, it has its own limitations. First, after the aneurysm is filled with the coils, it will remain its original size. As a result, the pressure on the surrounding tissue exerted by the aneurysm will not be removed. Second, this procedure is not very effective for wide-necked aneurysms, where the coil is likely to protrude into the parent vessels. This problem may be mitigated by using a stent in combination with coiling embolization, but the procedure is difficult and time-consuming.

BRIEF SUMMARY OF THE INVENTION

Using a self-expanding tube, sometimes referred to as a stent, alone to treat the aneurysm is a promising way to avoid the problems stated above. In this method, a tube with an area of relatively low porosity is placed across the aneurysm neck in such a way as to redirect blood flow away from the sac and trigger formation of a thrombus within the aneurysm. Because the aneurysm solidifies naturally on itself, there is less danger of its rupture. Furthermore, because no coil is involved in this method, the aneurysm will gradually shrink as the thrombus is absorbed. Consequently, the pressure applied on the surrounding tissue can be removed. It is difficult, however, to deploy a self-expanding tube optimally in this context. The tube has to be flexible enough to pass through and adapt to the shape of the very tortuous blood vessels in the brain while at the same time providing sufficient coverage (low porosity) to redirect blood flow away from the aneurysm to an adequate extent. The tube needs to be deployed reliably and controllably, with a minimal risk of damage to the tube or surrounding tissue.

It is an object of the invention to provide apparatus and methods for improving the process of deploying a self-expanding tube, particularly in the context of treating an intracranial aneurysm.

According to an aspect of the invention, there is provided a delivery system for deploying a self-expanding tube into a blood vessel, comprising: a tubular member configured for insertion into the blood vessel; an elongate body extending within a lumen of the tubular member; and a self-expanding tube positioned radially between the tubular member and the elongate body, wherein: over at least 50% of the length of the self-expanding tube, at least a portion of the self-expanding tube engages outwardly with the tubular member and inwardly with the elongate body; and a longitudinal engagement force acting between the self-expanding tube and the tubular member and a longitudinal engagement force acting between the self-expanding tube and the elongate body are such that, during all stages of deployment of the self-expanding tube in use by longitudinal retraction of the tubular member relative to the elongate body, there is substantially no relative movement longitudinally between the elongate body and any portion of the self-expanding tube that remains in engagement with the elongate body.

By distributing a strong longitudinal engagement between the tube and the elongate body over a large proportion of the length of the tube it is possible to reliably deploy tubes with a minimal risk of damage to their structural integrity even in the case where the tubes have low longitudinal stiffness. Alternative techniques based on engaging with the tube only in localised regions (e.g. by pushing from one end or pulling from the other end) are likely to damage tubes having low longitudinal stiffness. Delivery systems according to embodiments of the present disclosure thus widen the range of self-expanding tubes that can be delivered reliably, opening up in particular the possibility of reliably deploying stents of low longitudinal stiffness.

In an embodiment, the elongate body is configured to self expand from a radially contracted state to a radially expanded state in a process involving longitudinal shortening of the elongate body relative to the longitudinal axis of the tubular member. This causes the elongate body to contract as the tube is being deployed, thereby reducing or avoiding extension of the elongate body longitudinally beyond the tube during deployment and reducing or avoiding risk of injury by the elongate body.

BRIEF DESCRIPTION OF THE SEVERAL VIEWS OF THE DRAWINGS

Embodiments of the invention will now be described, by way of example only, with reference to the accompanying drawings in which corresponding reference symbols indicate corresponding parts, and in which.

DETAILED DESCRIPTION OF THE INVENTION

Embodiments of the present disclosure provide a delivery system 2 for deploying a self-expanding tube 6 into a blood vessel. The tube 6 may be referred to as a stent. In a preferred embodiment the tube 6 is configured to be positioned across the opening of an aneurismal sac to redirect blood flow away from the aneurismal sac. The redirection of blood flow is preferably sufficient to promote thrombus formation within the sac.

Figure 1:
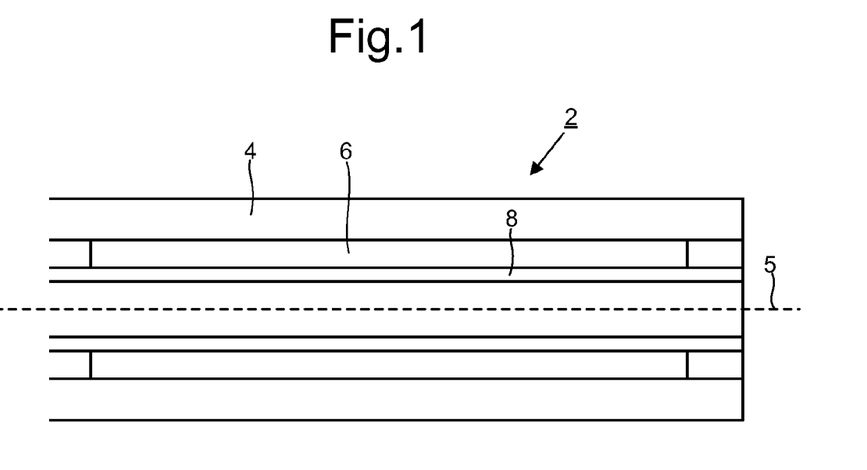
FIG. 1 is a schematic side sectional view of a distal portion of a delivery system for deploying a self-expanding tube into a blood vessel.
Figure 2:
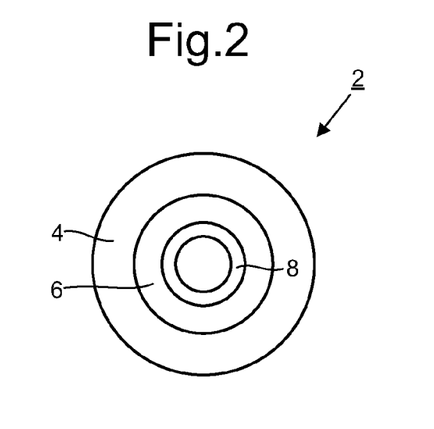
FIG. 2 is a schematic end sectional view of the delivery system of FIG. 1.

The delivery system 2 comprises a tubular member 4 configured for insertion into the blood vessel. A distal end of the tubular member 4 is depicted in FIGS. 1 and 2. Tubular members 4 configured for such use are well known in the art of minimally invasive surgery. The tubular member 4 will typically be cylindrical and dimensioned such that its distal end can be brought to the region to be treated with the body. In the case of treating a cerebral aneurysm, the tubular member 4 will be configured so that it can be navigated to the opening of the aneurismal sac within the vasculature of the brain.

The delivery system 2 further comprises an elongate body 8 extending within a lumen of the tubular member 4. The elongate body 8 may be hollow or solid. In an embodiment, the elongate body 8 is a wire.

A self-expanding tube 6 to be deployed by the delivery system 2 is positioned radially between the tubular member 4 and the elongate body 8. The self-expanding nature of the tube 6 causes the tube 6 to engage (i.e. press) outwardly against the tubular member 4. Additionally, over at least a defined length of the tube 6, at least a portion of the tube 6 engages inwardly with the elongate body 8. Thus, over at least the defined length of the tube 6, at least a portion of the tube 6 engages (e.g. is in direct or indirect contact in the radial direction) both with the tubular member 4 and with the elongate body 8. In an embodiment the defined length is 50%, optionally 60%, optionally 70%, optionally 80%, optionally 90%, optionally 95%, optionally substantially all, of the length of the tube 6.

The deployment of the tube 6 is achieved by longitudinal retraction of the tubular member 4 relative to the elongate body 8, which allows the tube 6 to self expand outwardly and leave the delivery system. The tubular member 4 and the elongate body 8 are configured such that a longitudinal engagement force (e.g. friction) acting between the tube 6 and the tubular member 4 and a longitudinal engagement force (e.g. friction) acting between the tube 6 and the elongate body 8 are such that, during all stages of deployment of the tube 6 there is substantially no relative movement longitudinally between the elongate body 8 and any portion of the tube 6 that remains in engagement with the elongate body 8. To achieve the required functionality the longitudinal engagement force between the tubular member 4 and the tube 6 is weaker than the longitudinal engagement force between the tube 6 and the elongate body 8 at each position along the length of the tube 6. At it simplest this may be implemented by providing a relatively low friction connection between the tube 6 and the tubular member 4 and a relatively high friction connection between the tube 6 and the elongate body 8. Other possibilities are available, however, as described below.

The engagement between the tubular member 4 and the tube 6 may be via direct contact between these two elements or via an intermediate element, such as a coating or other structure. The engagement between the tube 6 and the elongate body 8 may be via direct contact between these elements or via an intermediate element such as a coating or structure.

By distributing a strong longitudinal engagement between the tube and the elongate body over a large proportion of the length of the tube it is possible to reliably deploy tubes with a minimal risk of damage to their structural integrity even in the case where the tubes have low longitudinal stiffness. Alternative techniques based on engaging with the tube only in localised regions (e.g. by pushing from one end or pulling from the other end) are likely to damage tubes having low longitudinal stiffness. Delivery systems according to embodiments of the present disclosure thus widen the range of self-expanding tubes that can be delivered reliably, opening up in particular the possibility of reliably deploying stents of low longitudinal stiffness.

The ability of the present delivery system to handle tubes 6 with low longitudinal stiffness provides greater flexibility in how the tubes 6 can be designed, allowing the tubes 6 to be optimised for other properties (e.g. for radial compressibility, flexibility, and/or low porosity in the deployed state). For example, the absence of a requirement for high longitudinal stiffness facilitates design of a tube that can extend by a large amount in the longitudinal direction, which facilitates simultaneously providing high radial compressibility during delivery and low porosity in the deployed state. This can be understood as follows.

The term porosity, $\rho$, refers to the ratio of the surface area of open regions to the total external surface area occupied by material of the self-expanding tube 6, for example a frame of interconnecting arms. The total external surface area is the sum of the surface area of the open regions and the surface area of the regions occupied by the material of the frame. When the frame is cylindrical, the total external surface area is simply $2\pi.R.L$, where R is the radius of the cylinder and L is the length of the cylinder.

Consider a frame with a porosity $\rho$ in the fully radially expanded state. If the radius and length of the frame in the fully radially expanded state are $R_0$ and $L_0$, respectively, the minimum radius $R_{min}$ that the frame can achieve in the radially contracted state, defined by the state in which the porosity becomes zero, is governed by $$R_{min} = \frac{(1-\rho)L_0}{L_1} \cdot R_0$$

where $L_1$ is the length of the frame in the radially contracted state. This relationship assumes that elements of the frame are not allowed to overlap with each other in the radial direction.

This relationship illustrates that if the length of the frame is not allowed to change to any significant extent, the radius can only reduce by a factor of $\rho$. As $\rho$ needs to be quite low (e.g. less than 80%, at least in a low porosity region, such as a region intended for positioning in use over the opening to an aneurismal sac), this represents a significant limitation to the extent to which the tube can be narrowed for delivery to a region of interest. For example, if the porosity $\rho$ of the frame is 20% and the length of the frame is not allowed to change during radial contraction, i.e. $L_1=L_0$, the frame can achieve only a maximum 20% reduction in radius. The provision of a frame that can expand longitudinally when adopting the radially contracted state is based on this understanding and allows much greater reductions in radius to be achieved. For example, if the length is allowed to double, i.e. $L_1=2.L_0$, the frame can achieve a 60% reduction in radius for a porosity of 20%.

In an embodiment, the longitudinal shortening of the tube 6 comprises a shortening of at least 20%, optionally at least 30%, optionally at least 50%, optionally at least 75%, in a direction parallel to the longitudinal axis 5 of the tubular member 4, between a state in which the tube 6 is fully within the tubular member 4 (radially) to a state in which the tube 6 has fully left the tubular member 4 (and has expanded).

Figure 3:
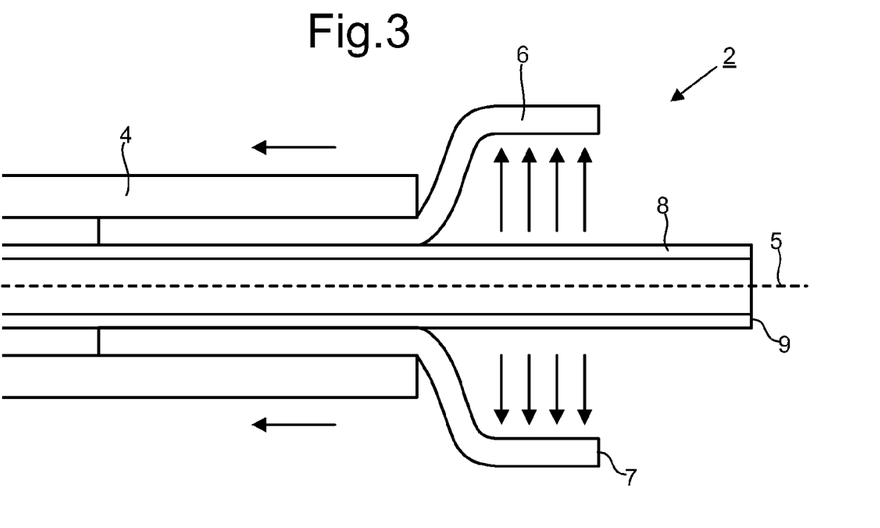
FIG. 3 is a schematic side sectional view depicting a stage of deployment of a self-expanding tube in which a tubular member is longitudinally retracted relative to an elongate body.
Figure 4:
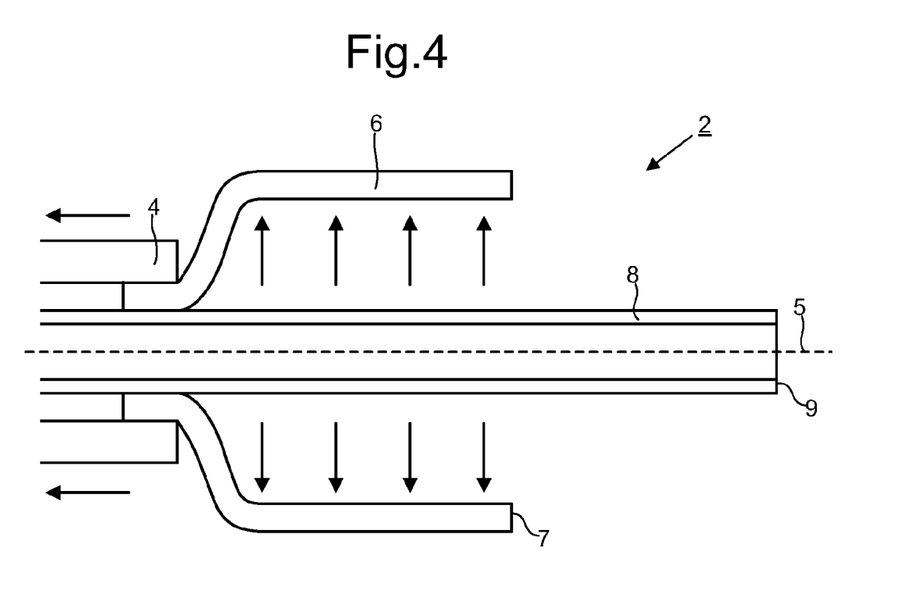
FIG. 4 depicts a stage of deployment subsequent to the stage depicted in FIG. 3, with the tube almost fully deployed.

FIGS. 3 and 4 depict stages in an example deployment procedure using the delivery system 2 according to an embodiment. FIG. 3 depicts the delivery system 2 of FIGS. 1 and 2 after the tubular member 4 has been retracted longitudinally relative to the elongate body 8 (indicated by the arrows showing relative movement to the left). The relative movement can be provided by holding the elongate body 8 stationary and retracting the tubular member 4, by holding the tubular member 4 stationary and advancing the elongate body 8 or a combination of the two. As the tubular member 4 is retracted, a growing distal region of the tube 6 becomes no longer constrained radially and expands outwards. As the tube 6 expands outwards it also shortens longitudinally. This results in a distal end 9 of the elongate body 8 ending up protruding further from the tubular member 4 than a distal end 7 of the tube 6. As the deployment procedure continues, as depicted in FIG. 4, more and more of the tube 6 reaches the expanded state, while the degree to which the distal end 9 of the elongate body 8 protrudes ahead of the distal end 7 of the tube 6 also increases.

Figure 5:
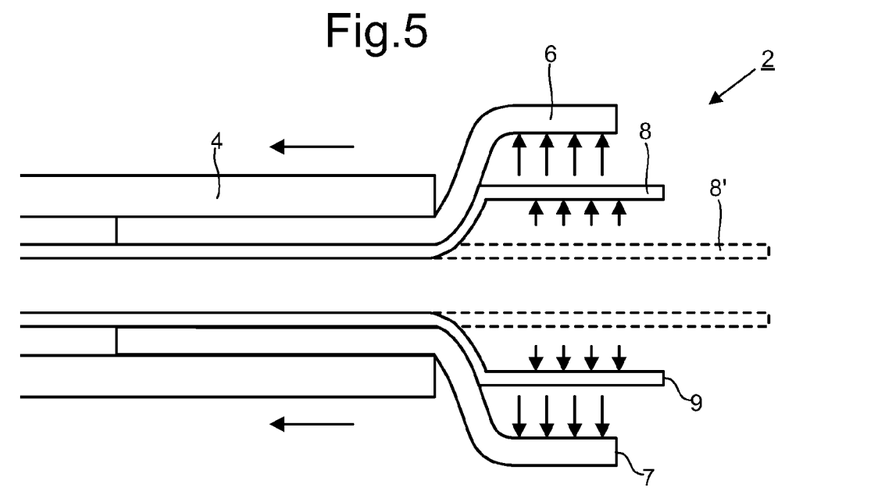
FIG. 5 is a schematic side sectional view depicting a stage of deployment of a self-expanding tube in which a tubular member is longitudinally retracted relative to an elongate body in the case where the elongate body is self-expanding.
Figure 6:
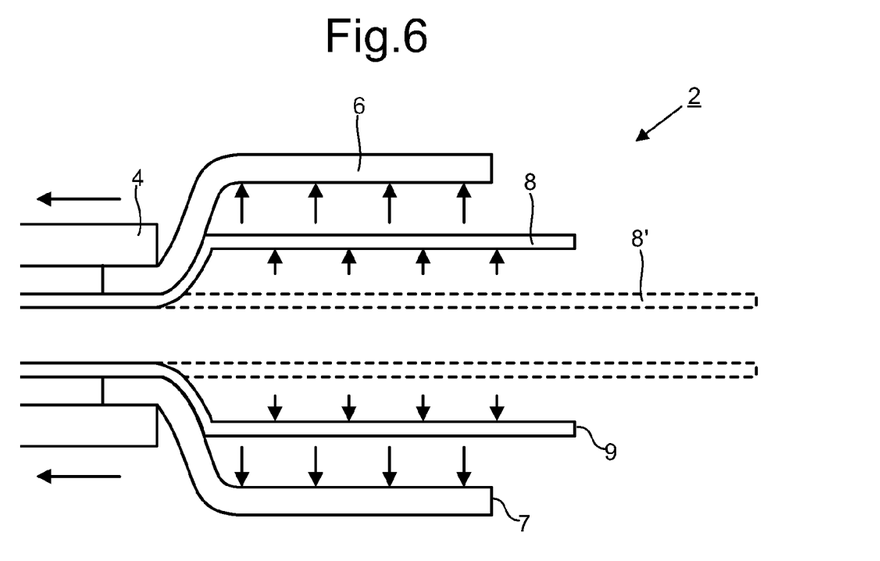
FIG. 6 depicts a stage of deployment subsequent to the stage depicted in FIG. 5, with the tube almost fully deployed.

The protrusion of the elongate body 8 ahead of the deployed tube 6 discussed above may be undesirable. There may for example be a risk of the elongate body 8 advancing undesirably into tissue and causing injury. This risk may be mitigated by configuring the elongate body 8 to be relatively soft and pliable. However, this may limit the range of materials that can be used for the elongate body 8. In an embodiment, the issue is addressed by arranging for the elongate body 8 itself to also self expand from a radially contracted state to a radially expanded state in a process involving longitudinal shortening of the elongate body 8 relative to the longitudinal axis 5 of the tubular member 4. The behaviour of an example delivery system 2 configured in this way is depicted in FIGS. 5 and 6, which depict stages in a deployment procedure corresponding to the stages discussed above with reference to FIGS. 3 and 4. For ease of comparison with the delivery system 2 of FIGS. 3 and 4, broken lines are used to depict the configuration of the elongate body 8' in the example of FIGS. 3 and 4 at each of the two corresponding stages. FIG. 5 shows how the tube 6 expands outwardly as before and contracts longitudinally. Unlike in the example of FIGS. 3 and 4, however, the elongate body 8 also expands radially outwardly and retracts longitudinally. The distal end 9 of the elongate body 8 is thus significantly less extended than in the corresponding stage in FIG. 3. As the procedure progresses, as depicted in FIG. 6, the elongate body 8 continues to retract longitudinally, leading to an overall degree of protrusion in the longitudinal direction relative to the deployed tube 6 that is significantly less than in the delivery system 2 of FIGS. 3 and 4.

The self expanding properties of the elongate body 8 may be provided in various ways. Unlike the tube 6, which needs to have specific properties to perform its function in the deployed state (e.g. low porosity), the requirements for the elongate body 8 are more relaxed. Any of a wide variety of configurations known for self-expanding stents for general application may be used, for example.

In an embodiment, the elongate body 8 is formed from a material having a shape memory property, such as a shape memory alloy (e.g. nitinol). The elongate body 8 may be formed exclusively from a shape memory material, or from a composite of shape memory material and other materials. For example, the elongate body 8 may have an inner portion of shape memory material and an outer portion of non-shape memory material, or an outer portion of shape memory material with an inner core of non-shape memory material. This can allow greater flexibility in choosing the properties of the elongate body, for example to choose the frictional properties of the surface of the elongate body in contact with the tube.

The elongate body 8 self expands and longitudinally shortens by switching from a state in which a longitudinal axis of the elongate body 8 is parallel to the longitudinal axis 5 of the tubular member 4 to a state in which the longitudinal axis of the elongate body 8 is not parallel to the longitudinal axis 5 of the tubular member 4, due to shape memory forces. For example, at least a portion of the elongate body 8 may adopt a smooth non-planar space curve, such as a helix, in the radially unconstrained state. An example of this type is depicted schematically in FIG. 7.

The elongate body 8 may also adopt other shapes, for example a planar curve or shapes without smooth curves, as long as adopting such shapes results in longitudinal contraction (relative to the longitudinal axis 5 of the tubular member 4) of the elongate body 8.

Figure 7:
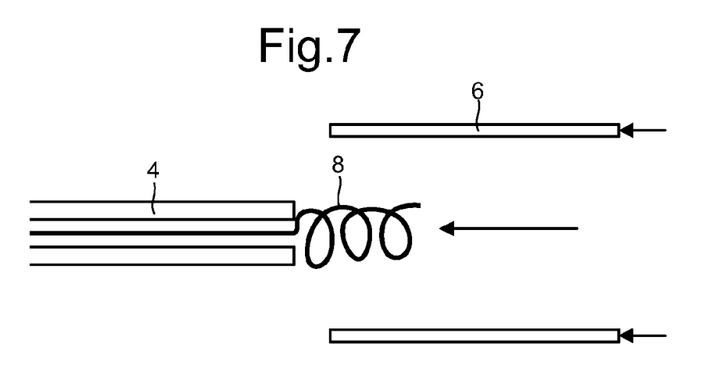
FIG. 7 is a schematic side sectional view depicting deployment of a self-expanding tube from a delivery system comprising an elongate member configured to self expand into a helical shape.

The longitudinal shortening of the elongate body 8 comprises a shortening of at least 5%, optionally at least 10%, optionally at least 20%, optionally at least 30%, optionally at least 50%, optionally at least 75% of the portion of the elongate body 8 that has moved longitudinally outside of the tubular member 4. In an embodiment, the longitudinal shortening of the elongate body 8 is less than the longitudinal shortening of the tube 6, as depicted in FIGS. 5 and 6. Alternatively, the longitudinal shortening of the elongate body 8 may be equal to or greater than the longitudinal shortening of the tube 4 (as shown in FIG. 7). In this latter case, there is substantially no protrusion of the elongate body 8 relative to the tube 6, thereby minimising risk of injury by movement of the elongate body 8 relative to tissue during the deployment process.

The higher engagement between the elongate body 8 and the tube 6 relative to the engagement between the tubular member 4 and the tube 6 may be achieved in a variety of ways. As mentioned above, frictional properties of the surfaces contact with the tube 6 may be selected accordingly. Alternatively or additionally, in an embodiment an outer portion of the elongate body 8 is configured to deform locally when pressed against the tube 6. The elongate body 8 may, for example, be provided with a pliable outer coating 10 or may itself be formed from a pliable material. The local deformation causes material forming the outer portion of the elongate body 8 to protrude radially into interstices of the tube 6 (e.g. gaps between interconnected arms of a frame of the tube 6), thereby increasing the longitudinal engagement force between the tube 6 and the elongate body 8.

Figure 8:
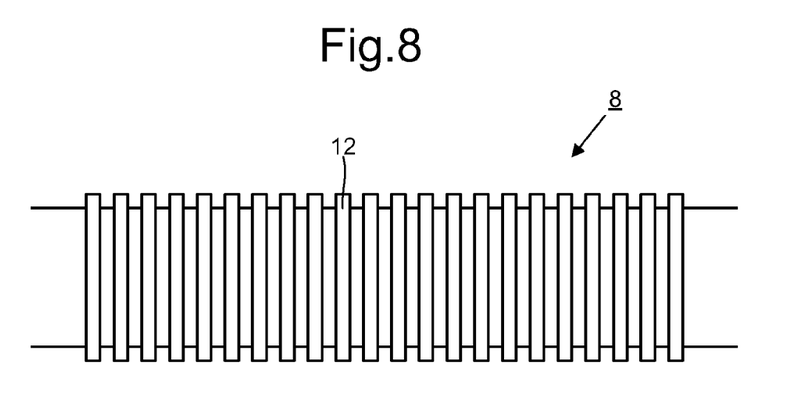
FIG. 8 is a schematic side view of an elongate body having a plurality of preformed protrusions on a plurality of ring elements.
Figure 9:
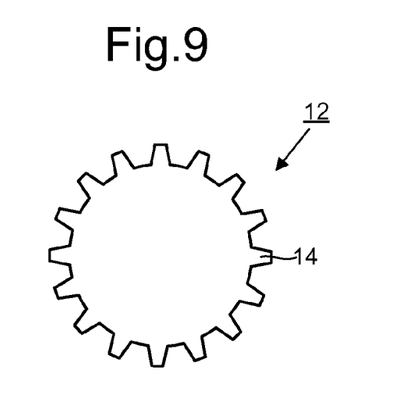
FIG. 9 is a schematic end sectional view through one of the ring elements of FIG. 8.

Alternatively or additionally, the outer surface of the elongate body 8 may be provided with a plurality of preformed or rigid protrusions 14, as depicted schematically in FIGS. 8 and 9. The protrusions 14 engage in use with interstices of the tube 6 and thereby increasing the longitudinal engagement force acting between the tube 6 and the elongate body 8. The preformed protrusions may be formed by moulding, for example. In an embodiment, the outer surface of the elongate body 8 is formed from a material which is soft above a predetermined temperature, the tube 6 is positioned against the elongate body 8 while the surface is soft, thereby forming the protrusions, and the assembly is allowed to cool until the protrusions harden and become rigid (self-supporting). In the particular example shown in FIGS. 8 and 9, the protrusions 14 are provided via a plurality of ring elements 12 that are each provided with protrusions 14 spaced regularly along the circumference of the ring element 12. It will be appreciated, however, that many other configurations could be used.

In one embodiment, either or both of a composition and surface texture of the inner surface of the tubular member 4 is or are arranged to be uniform over a length in which the tubular member 4 is in contact with the tube 6. Optionally, a low friction coating may be provided on the inner surface of the tubular member 4.

For ease of manufacture, the elongate body 8 may also be configured such that either or both of a composition and surface texture of the outer surface of the elongate body 8 is uniform over a length in which the elongate body 8 is in contact with the tube 6. Even where the surface is uniform, it would be straightforward for the skilled person to arrange for the friction to be higher than the friction provided by the tubular member 4, for example by providing a suitable high friction coating or surface roughening.

The delivery system 2 of embodiments of the present disclosure is particularly applicable to deploying self-expanding tubes 6 having low porosities, preferably porosities less than 80%, optionally less than 70%, optionally less than 60%, optionally less than 50%, when deployed in the self-expanded state. Such porosities are effective for redirecting blood flow away from an aneurismal sac when the self-expanding tube is deployed over the opening of the aneurismal sac. The self-expanding tube 6 may comprise an elongate frame. The frame may comprise a shape memory alloy, for example, such as nitinol. Alternatively, the frame may comprise a stainless steel, polymer or other biocompatible material. The frame may comprise a network of interconnecting arms. The frame may be formed for example by laser cutting a hollow tube, by 3D printing, or by other techniques known in the art for manufacturing such structures. All of the interconnecting arms may be provided at the same radius and without any overlaps in the radial direction.

The delivery system 2 may be used according to preferred embodiments as part of a method for delivering a self-expanding tube into a blood vessel for the purpose of redirecting blood flow away from an aneurismal sac.

We claim:

1. A delivery system for deploying a self-expanding tube into a blood vessel, comprising:
    a tubular member configured for insertion into the blood vessel;
    an elongate body extending within a lumen of the tubular member; and
    a self-expanding tube positioned radially between the tubular member and the elongate body, wherein:
    over at least 50% of the length of the self-expanding tube, at least a portion of the self-expanding tube engages outwardly with the tubular member and inwardly with the elongate body;
    a longitudinal engagement force acting between the self-expanding tube and the tubular member and a longitudinal engagement force acting between the self-expanding tube and the elongate body are such that, during all stages of deployment of the self-expanding tube in use by longitudinal advancement of the elongate body relative to the tubular member, there is substantially no relative movement longitudinally between the elongate body and any portion of the self-expanding tube that remains in engagement with the elongate body;
    wherein the self-expanding tube is configured to self expand from a radially contracted state to a radially expanded state in a process involving longitudinal shortening of the self-expanding tube relative to a longitudinal axis of the tubular member;
    wherein the elongate body is configured to self expand from a radially contracted state to a radially expanded state in a process involving longitudinal shortening of the elongate body relative to the longitudinal axis of the tubular member; and
    wherein the elongate body is formed from a material having a shape memory property and the elongate body is configured to self-expand and longitudinally shorten by switching from a state in which a longitudinal axis of the elongate body is parallel to the longitudinal axis of the tubular member to a state in which the longitudinal axis of the elongate body is not parallel to the longitudinal axis of the tubular member due to shape memory forces.

2. The delivery system of claim 1, wherein the longitudinal shortening of the self-expanding tube comprises a shortening of at least 20% in a direction parallel to the longitudinal axis of the tubular member, between a state when the self-expanding tube is fully within the tubular member to a state when the self-expanding tube has fully left the tubular member.

3. The delivery system of claim 1, wherein the elongate body adopts a smooth non-planar space curve in an unconstrained state outside of the tubular member.

4. The delivery system of claim 3, wherein the smooth non-planar space curve comprises a helix.

5. The delivery system of claim 1, wherein the longitudinal shortening of the elongate body comprises a shortening of at least 5% of the portion of the elongate body that has moved longitudinally outside of the tubular member.

6. The delivery system of claim 1, wherein the longitudinal shortening of the elongate body is greater than the longitudinal shortening of the self-expanding tube.

7. The delivery system of claim 1, wherein the elongate body has an inner portion and an outer portion, the outer portion engaging with the self-expanding tube, and one of the inner portion and the outer portion is formed from a material having a shape memory property and the other of the inner portion and the outer portion is formed from a material not having a shape memory property.

8. The delivery system of claim 1, wherein an outer portion of the elongate body is configured to deform locally when pressed against the self-expanding tube, such that material forming the outer portion of the elongate body protrudes radially into interstices of the self-expanding tube and thereby increases the longitudinal engagement force acting between the self-expanding tube and the elongate body.

9. The delivery system of claim 1, wherein an outer portion of the elongate body comprises a plurality of pre-formed or rigid protrusions that engage in use with interstices of the self-expanding tube and thereby increase the longitudinal engagement force acting between the self-expanding tube and the elongate body.

10. The delivery system of claim 1, configured such that either or both of a composition and surface texture of the inner surface of the tubular member is uniform over a length in which the tubular member is in contact with the self-expanding tube.

11. The delivery system of claim 1, configured such that either or both of a composition and surface texture of the outer surface of the elongate body is uniform over a length in which the elongate body is in contact with the self-expanding tube.

12. The delivery system of claim 1, wherein the self-expanding tube has a porosity when deployed such that blood flow is redirected away from an aneurismal sac when the self-expanding tube is deployed over the opening of the aneurismal sac.

13. The delivery system of claim 1, wherein the self-expanding tube is configured to redirect blood flow away from an aneurismal sac when deployed over an opening to the aneurismal sac.

14. A method of deploying a self-expanding tube into a blood vessel, comprising:
   using the delivery system of claim 1 to deploy the self-expanding tube by longitudinally advancing the elongate body relative to the tubular member until the self-expanding stent is released from the delivery system by self-expansion of the self-expanding tube.

* * * * *